US011324807B2

(12) United States Patent
Florin-Robertsson et al.

(10) Patent No.: US 11,324,807 B2
(45) Date of Patent: May 10, 2022

(54) COMPOSITIONS COMPRISING ANAKINRA

(71) Applicant: Swedish Orphan Biovitrum AB (publ), Stockholm (SE)

(72) Inventors: Ebba Florin-Robertsson, Stockholm (SE); Jonas Fransson, Uppsala (SE); Barry D. Moore, Killearn (GB)

(73) Assignee: Swedish Orphan Biovitrum AB (publ), Stockholm (SE)

(*) Notice: Subject to any disclaimer, the term of this patent is extended or adjusted under 35 U.S.C. 154(b) by 488 days.

(21) Appl. No.: 15/569,659

(22) PCT Filed: Apr. 27, 2016

(86) PCT No.: PCT/EP2016/059398
§ 371 (c)(1),
(2) Date: Oct. 26, 2017

(87) PCT Pub. No.: WO2016/174082
PCT Pub. Date: Nov. 3, 2016

(65) Prior Publication Data
US 2018/0110836 A1  Apr. 26, 2018

(30) Foreign Application Priority Data
Apr. 28, 2015 (EP) ................................. 15165421

(51) Int. Cl.
| | |
|---|---|
| *A61K 38/20* | (2006.01) |
| *A61K 9/00* | (2006.01) |
| *A61K 47/18* | (2017.01) |
| *A61K 47/20* | (2006.01) |
| *A61P 27/02* | (2006.01) |
| *A61P 27/14* | (2006.01) |
| *A61P 27/04* | (2006.01) |
| *A61K 47/02* | (2006.01) |
| *A61K 47/12* | (2006.01) |
| *A61K 47/22* | (2006.01) |
| *A61K 47/26* | (2006.01) |

(52) U.S. Cl.
CPC ........ *A61K 38/2006* (2013.01); *A61K 9/0048* (2013.01); *A61K 47/02* (2013.01); *A61K 47/12* (2013.01); *A61K 47/183* (2013.01); *A61K 47/20* (2013.01); *A61K 47/22* (2013.01); *A61K 47/26* (2013.01); *A61P 27/02* (2018.01); *A61P 27/04* (2018.01); *A61P 27/14* (2018.01)

(58) Field of Classification Search
CPC .. A61K 2300/00; A61K 47/26; A61K 9/0048; A61K 38/2006; A61K 47/183; A61K 47/02; A61K 47/12; A61K 47/20; A61K 47/22; A61K 38/20; A61P 27/02
See application file for complete search history.

(56) References Cited

U.S. PATENT DOCUMENTS

| | | | |
|---|---|---|---|
| 6,858,409 B1* | 2/2005 | Thompson | C07K 14/47 435/252.3 |
| 2010/0297117 A1* | 11/2010 | Sloey | A61K 9/0019 424/133.1 |
| 2011/0182898 A1* | 7/2011 | Karrer | C07K 14/70521 424/134.1 |
| 2014/0018298 A1* | 1/2014 | Fransson | A61K 38/1793 514/16.6 |
| 2014/0314746 A1 | 10/2014 | Artlett et al. | |

FOREIGN PATENT DOCUMENTS

| | | |
|---|---|---|
| WO | WO 2005/097195 A2 | 10/2005 |
| WO | WO 2009/025763 A2 | 2/2009 |
| WO | WO 2012/108828 A1 | 8/2012 |
| WO | WO 2014/160371 A1 | 10/2014 |

OTHER PUBLICATIONS

Ugwu, S.O. et al. The effect of buffers on protein conformatinal stabiltiy. Pharmaceutical Technology, Mar. 2004, p. 86-113.*
International Search Report and Written Opinion dated Jul. 26, 2016 for Application No. PCT/EP2016/059398.
Amparo et al., Topical interleukin 1 receptor antagonist for treatment of dry eye disease: a randomized clinical trial. JAMA Ophthalmol. Jun. 2013;131(6):715-723. doi: 10.1001/jamaophthalmol.2013.195.
Liebner et al., Head to head comparison of the formulation and stability of concentrated solutions of HESylated versus PEGylated anakinra. J Pharm Sci. Feb. 2015; 104(2):515-26. doi: 10.1002/jps. 24253. Epub Dec. 1, 2014.

* cited by examiner

*Primary Examiner* — Prema M Mertz
(74) *Attorney, Agent, or Firm* — Wolf, Greenfield & Sacks, P.C.

(57) ABSTRACT

The present invention relates to compositions comprising anakinra, buffer, and optionally at least one osmolyte and optionally further excipients. Further, the present invention relates to use of said compositions for treatment of for example ophthalmic disorders.

31 Claims, 2 Drawing Sheets

COMPOSITIONS COMPRISING ANAKINRA

CROSS-REFEENCE TO RELATED APPLICATIONS

This application is the U.S. National Stage, pursuant to 35 U.S.C. § 371, of International Application No. PCT/EP2016/059398, filed Apr. 27, 2016, designating the United States and published on Nov. 3, 2016 as Publication WO 2016/174082, which claims the benefit of European Patent Application No. 15165421.7, filed Apr. 28, 2015, the entire contents of which are incorporated herein by reference.

FIELD OF THE INVENTION

The present invention relates to compositions comprising anakinra, buffer, and optionally at least one osmolyte and optionally further excipients. Further, the present invention relates to use of said compositions for treatment of ophthalmic disorders.

BACKGROUND OF THE INVENTION

The Interleukin-1 family is a group of proteins involved in regulating immune and inflammatory responses. Members of the group mediate a range of diseases, such as rheumatoid arthritis, inflammatory bowel disease, asthma, diabetes, leukemia, and psoriasis.

Anakinra is a recombinant form of a naturally occurring Interleukin-1 receptor antagonist (IL-1ra) protein, functioning as a competitive inhibitor for receptor binding of IL-1. IL-1ra has a balancing function with regard to other pro-inflammatory variants of IL-1 (Clin. Therapeutics 2004, 26, 1960-1975). A deficiency of IL-1ra could thus be a risk factor for a number of autoimmune diseases. Symptoms of those diseases may be alleviated by treatment with anakinra.

Components in a protein drug formulation may include buffering agents, tonicity agents, antioxidants, stabilizers, surfactants, bulking agents, chelating agents and preservatives. Kineret®, a formulation of anakinra at pH 6.5 suitable for injection, contains sodium citrate, sodium chloride, disodium EDTA, polysorbate 80 and water. The selection of sodium citrate as buffer component for anakinra in the Kineret® formulation was based on detailed studies evaluating the short and long term stability of anakinra. Several potential buffer components were evaluated, sodium phosphate being one, and sodium citrate was identified as providing the optimal stability with respect to anakinra aggregation (WO 2005/097195). Aggregation of anakinra was a major concern for the selection of the buffer component, stabilizers and storage temperature. The concentration of the sodium citrate was minimized as much as possible considering its known local irritating effect upon injection.

Anakinra has also been formulated without sodium citrate in order to avoid reported issues with local tolerance at the subcutaneous injection site (WO 2012/108828). The appropriate components in a protein drug formulation, and their respective levels, are determined by for example the intended use.

Liquid drug products of biological molecules with a pre-specified composition and pH can be manufactured by various processes. The most common way is to prepare stock solutions with specified compositions and pH and then mix these together to obtain a vehicle. The vehicle is then mixed with the active protein in an aqueous solution to a final composition with a pre-defined pH.

IL-1 also plays a role in a number of eye disorders such as the initiation and maintenance of the inflammation and pain associated with dry eye disease and the redness and itching associated with allergic conjunctivitis. It has been shown that IL-1ra may be able to prevent and treat certain IL-1 related eye disorders (WO 2009/025763, Amparo et al., JAMA Ophthalmology 2013, 131, 6, 715-723). In WO 2014/160371, stable formulations of an IL-1β/IL-1ra chimeric cytokine protein for topical administration in the eye are disclosed.

One challenge with protein drug formulations in general is the poor stability of the active protein. Hence, there is a need for an ophthalmic Interleukin-1 receptor antagonist formulation with improved stability.

DESCRIPTION OF THE INVENTION

It is an object of the present invention to provide novel anakinra compositions with improved stability.

Another object of the present invention is to provide novel anakinra compositions suitable for use in therapy, such therapy preferably including topical administration of such anakinra compositions.

Another object of the present invention is to provide novel anakinra compositions with with low concentrations of anakinra, such as from 0.01 mg/mL to 30 mg/mL anakinra.

BRIEF DESCRIPTION OF THE DRAWINGS

FIG. 1. shows anakinra monomer content in anakinra solutions after storage at 35° C. formulated in different concentrations of HEPES buffers, compared with anakinra solutions after storage at 35° C. formulated in citrate buffer.

A composition comprising anakinra and buffer as defined in this disclosure is advantageous in that it exhibits stability under certain conditions. Conditions that a commercial anakinra product may experience include long term storage under refrigerated conditions, short term storage under ambient conditions, and mechanical stress during transportation, all of these being conditions that the above composition has been developed to withstand.

With the term "anakinra" is meant a recombinant form of IL-1 receptor antagonist (IL-1ra) having the 152 amino acid sequence shown as positions 26-177 in NCBI Reference Sequence NP_776214.1 (www.ncbi.nlm.nih.gov). Further, the term "anakinra" should be understood as including modified forms of anakinra, e.g. amino acid variants having at least 90%, 95%, 97% or 99% identity with the anakinra amino acid sequence. The person skilled in the art will understand that many combinations of deletions, insertions, inversions and substitutions can be made within the anakinra amino acid sequence, provided that the resulting molecule ("the anakinra variant") is biologically active, e.g. possesses the ability to inhibit IL-1. Particular anakinra variants are described in e.g. U.S. Pat. Nos. 5,075,222; 6,858,409 and 6,599,873.

The term "anakinra" further includes fusion proteins comprising anakinra. Anakinra can be formatted to have a larger hydrodynamic size, for example, by attachment of polyalkyleneglycol groups (e.g. a polyethyleneglycol (PEG) group), serum albumin, transferrin, transferrin receptor or at least the transferrin-binding portion thereof, an antibody Fc region, or by conjugation to an antibody domain.

By "buffer" is meant a chemical entity used to prevent changes in pH. Use of a buffer constitutes a means of keeping pH at a nearly constant value in a wide variety of chemical applications. HEPES, or 4-(2-hydroxyethyl)-1-piperazineethanesulfonic acid, is a zwitterionic organic chemical buffering agent which provides the composition as disclosed herein with advantageous properties in comparison with other buffers. In particular, use of a HEPES buffer may provide a stable composition. Another buffer that may be used in the composition as described herein is sodium citrate buffer. Sodium citrate is the sodium salt of citric acid, and has previously been demonstrated to provide anakinra compositions for injection with improved stability. However, as demonstrated in the appended examples, sodium citrate in combination with HEPES surprisingly stabilizes compositions comprising anakinra at a concentration of about 2 to 30 mg/ml at certain conditions such as elevated storage temperatures. In particular, HEPES buffer alone, surprisingly stabilizes compositions comprising anakinra at a concentration of about 2 to 30 mg/ml at certain conditions such as elevated storage temperatures. HEPES buffer is a buffer known in the art, however, it is not generally used in the pharmaceurical field of topical administration of pharmaceutical agents to the eye.

There is, in one aspect of the invention, provided a composition, comprising:

0.01 mg/mL to 30 mg/mL anakinra;

buffer, selected from HEPES and a mixture of HEPES and sodium citrate;

and optionally at least one osmolyte.

In one embodiment of this aspect, said composition comprises at least one osmolyte.

In one embodiment of this aspect, said buffer is HEPES buffer.

In one embodiment of this aspect, said buffer stabilizes the pH of the composition at a pH of from 6 to 7.

In one embodiment of this aspect, there is provided a composition, comprising:

0.01 mg/mL to 30 mg/mL anakinra; buffer, selected from HEPES and a mixture of HEPES and sodium citrate, wherein said buffer stabilizes the pH of the composition at a pH of from 6 to 7; and optionally at least one osmolyte. Typically the concentration of anakinra is 0.05 mg/mL to 30 mg/mL, such as about 0.1 mg/mL to 30 mg/mL, such as about 0.5 mg/mL to 30 mg/mL, such as about 1 mg/mL to 30 mg/mL, such as about 1.5 mg/mL to 30 mg/mL, such as about 2 mg/mL to 30 mg/mL, such as about 5 mg/mL, such as about 10 mg/mL such as about 15 mg/mL such as about 20 mg/mL or such as about 25 mg/mL.

In one embodiment of this aspect, there is provided a composition, comprising:

2 mg/mL to 30 mg/mL anakinra; buffer, selected from HEPES and a mixture of HEPES and sodium citrate, wherein said buffer stabilizes the pH of the composition at a pH of from 6 to 7; and optionally at least one osmolyte.

In one embodiment of this aspect, said buffer is a mixture of sodium citrate and HEPES.

An osmolyte should in this context be understood as a chemical entity which has the potential to modify the osmolality of a solution and to provide a stabilizing effect. Osmolality is a colligative property which depends on the total number of moles of all dissolved entities in 1000 g of solvent. Non-limiting examples of osmolytes are L-proline; D-threonine; L-serine; myoinositol; maltitol; D-raffinose; pentahydrate; hydroxyproline; taurine; glycine betaine; sucrose; mannitol; L-proline; D-threonine; L-serine, and methionine.

In one embodiment of this aspect, said composition comprises at least one osmolyte. Said at least one osmolyte may be selected from taurine, proline, hydroxyproline, mannitol and methionine. In another embodiment, said at least one osmolyte is selected from taurine, proline, and hydroxyproline. In another embodiment, said at least one osmolyte is taurine. In another embodiment, said at least one osmolyte is hydroxyproline. In another embodiment, said at least one osmolyte represents a mixture of taurine and hydroxyproline.

In one embodiment of this aspect, said at least one osmolyte represents 15 mg/mL to 40 mg/mL taurine, such as 15, 20, 25, 30, 35 or 40 mg/mL taurine. Other embodiments include the taurine concentrations as set out in the examples.

In one embodiment of this aspect, said at least one osmolyte represents 15 mg/mL to 40 mg/mL hydroxyproline, such as 15, 20, 25, 30, 35 or 40 mg/mL hydroxyproline. Other embodiments include the hydroxyproline concentrations as set out in the examples.

In one embodiment of this aspect, said composition further comprises one or more of a chelating agent, surfactant and a tonicity regulator.

A "chelating agent" is a chemical entity which can form two or more separate coordinate bonds between a polydentate (multiple bonded) ligand and a single central atom. Usually these ligands are organic compounds, examples of which are synthetic aminopolycarboxylic acid, such as ethylene diamine tetraacetic acid (EDTA) and diethylene triamine pentaacetic acid (DPTA); phosphonates; natural agents, such as the porphyrin rings of chlorophyll and hemoglobin; polysaccharides; polynucleic acids; amino acids, such as glutamic acid and histidine; organic diacids such as malate, and polypeptides such as phytochelatin. In addition, many microbial species produce water-soluble pigments that serve as chelating agents, termed siderophores. For example, species of Pseudomonas are known to secrete pyochelin and pyoverdine that bind iron. Another example is enterobactin, produced by *E. coli,* which is the strongest chelating agent known. Citric acid has chelating properties and is therefore used to capture multivalent ions and accordingly as an example soften water in soaps and laundry detergents.

In one embodiment, said composition comprises a chelating agent. Said chelating agent may be selected from EDTA; DPTA; phosphonate; a natural chelating agent; a siderophore; a polysaccharide; a polynucleic acid; an amino acid; an organic diacid and a polypeptide. Specific examples of such chelating agents are defined above. In one embodiment of this aspect, said chelating agent is EDTA.

By the term "surfactant" is meant a compound that reduces the surface tension (or interfacial tension) between a liquid and a gas phase, between two liquids or between a liquid and a solid. Surfactants are amphiphilic, meaning they contain both hydrophobic groups and hydrophilic groups. Surfactants will diffuse in water and adsorb at interfaces between air and water or at the interface between oil and water, in the case where water is mixed with oil.

In one embodiment, said composition comprises at least one surfactant. Non-limiting examples of surfactants suitable for use in said composition include, but are not limited to, block polymers of ethylene oxide and propylene oxide, such as poloxamers which are triblock copolymers composed of a central chain of polypropylene oxide flanked by two chains of polyethylene oxide, an example of which is pluronic F68; sorbitan monolaurate; sorbitol ester; polyglycerol fatty acid ester; cocamide DEA lauryl sulfate; alkanolamide; polyoxyethylene propylene glycol stearate; polyoxyethylene lauryl ether; polyoxyethylene cetyl ether; polysorbate, such as polysorbate 80 (PS80, also known as polyoxyethylene sorbitan monooleate or Tween 80™) and polysorbate 20 (PS20); glycerol monostearate; glycerol distearate; sorbitol monopalmitate; polyoxyethylene sorbitan monooleate; polyoxyethylene sorbitan monolaurate and propylene glycol monostearate. In one embodiment, said surfactant is non-ionic. In one embodiment, said surfactant is selected from polysorbate 80 and pluronic F68. Preferably, said surfactant is polysorbate 80.

By the term "tonicity regulator" is generally meant an agent which adjusts the osmolality of a solution and more specifically an agent which adjusts the osmolality to an osmolality value near the osmolality value of a physiological fluid.

In one embodiment, said composition comprises one or more tonicity regulator(s). Suitable tonicity regulators include, but are not limited to: sodium chloride (NaCl), sorbitol; mannitol, sucrose, trehalose, or other sugars. In one embodiment of this aspect, said tonicity regulator is NaCl.

In one embodiment, said composition comprises EDTA as a chelating agent, polysorbate 80 as a surfactant and NaCl as a tonicity regulator.

In one embodiment of this aspect, said buffer stabilizes the pH of the composition at a pH of about 6.5. As explained elsewhere herein, the function of a buffer is to keep the pH at a nearly constant value. In this embodiment, the buffer thus keeps the pH of the composition at about 6.5.

In one embodiment of this aspect, there is provided a composition, wherein said composition has an osmolality of about 150 to 320 mOsmol/kg. When the osmolality of a solution is described as isotonic/hypertonic or hypotonic the denotation tonicity means that the osmotic pressure of the solution is related to that of a physiological solution. In general, an isotonic solution has an osmolality of approximately 280 to 320 mOsm/kg.

In one embodiment, said composition comprises an osmolyte, the concentration of which is adjusted to provide an isotonic composition. In particular, such a composition may have an osmolality of from 280 to 320 mOsmol/kg. Isotonic preparations are generally preferred for topical administrations since they typically tend to be less irritating than non-isotonic solutions. An isotonic composition, preferably having an osmolality in the defined interval, is suitable for ocular administration, since its osmolality is within the same range as the osmolality of the eye.

However, hypotonic compositions may also be useful for ocular administration. Consequently, in one embodiment said composition comprises an osmolyte, wherein the concentration of said osmolyte is adjusted to provide a hypotonic composition. In particular, such a composition may have an osmolality of from 150 to 280 mOsmol/kg. A hypotonic composition may provide advantageous properties when administered to the eye of a patient, in particular if said patient experiences dry eye(s). The composition may then provide relief to the patient by moistening the eye.

In one embodiment, the composition comprises further ingredients, such as one or more preservative(s). A preservative may be added to a composition in order to for example maintain its microbiological safety.

In one embodiment of this aspect, said composition comprises:
- 2 mg/mL to 25 mg/mL anakinra;
- 5 mM to 50 mM HEPES buffer, wherein said buffer stabilizes the pH of the composition at a pH of from 6 to 7; and
- 1 mg/mL to 100 mg/mL of an osmolyte selected from taurine and hydroxyproline.

In one embodiment of this aspect, said composition comprises:
- 2 mg/mL to 25 mg/mL anakinra;
- 5 mM to 50 mM HEPES buffer, wherein said buffer stabilizes the pH of the composition at a pH of from 6 to 7;
- 1 mg/mL to 100 mg/mL of an osmolyte selected from taurine, proline, hydroxyproline, mannitol and methionine;
- 0.05 mM to 1 mM EDTA;
- 0.01% to 1% polysorbate 80; and
- 0.1 mg/mL to 5 mg/mL NaCl.

Compositions as defined above have been subjected to stability tests and have in such tests displayed beneficial properties.

In one embodiment of this aspect, said composition comprises:
- 2 mg/mL to 25 mg/mL anakinra;
- 5 mM to 50 mM HEPES buffer, wherein said buffer stabilizes the pH of the composition at pH from 6 to 7;
- 1 mg/mL to 50 mg/mL of an osmolyte selected from taurine, proline and hydroxyproline;
- 0.05 mM to 1 mM EDTA;
- 0.01% to 1% polysorbate 80; and
- 0.1 mg/mL to 5 mg/mL NaCl.

Compositions as defined above have been subjected to stability tests and have in such tests displayed good properties.

In one embodiment of this aspect, said buffer is from about 5 mM to about 15 mM HEPES buffer. Said HEPES buffer may further stabilize the pH of the composition at about 6.5.

In one embodiment of this aspect, said buffer is about 10 mM HEPES buffer. Said HEPES buffer may further stabilize the pH of the composition at about 6.5.

In one embodiment of this aspect, said composition comprises:
- 2 mg/mL to 25 mg/mL anakinra;
- a mixture of 5 mM to 50 mM HEPES buffer and 0.05 mM to 2 mM sodium citrate buffer, wherein said mixture buffer stabilizes the pH of the composition at a pH of from 6 to 7;
- 1 mg/mL to 100 mg/mL of an osmolyte selected from taurine, proline, hydroxyproline, mannitol and methionine;
- 0.05 mM to 1mM EDTA;
- 0.01% to 1% polysorbate 80; and
- 0.1 mg/mL to 5 mg/mL NaCl.

Compositions as defined above have been subjected to stability tests and have in such tests displayed good properties.

In one embodiment of this aspect, said composition comprises:
2 mg/mL to 25 mg/mL anakinra;
a mixture of 5 mM to 50 mM HEPES buffer and 0.05 mM to 2 mM sodium citrate buffer, wherein said mixture buffer stabilizes the pH of the composition at a pH of from 6 to 7;
1 mg/mL to 50 mg/mL of an osmolyte selected from taurine, proline and hydroxyproline;
0.05 mM to 1 mM EDTA;
0.01% to 1% polysorbate 80; and
0.1 mg/mL to 5 mg/mL NaCl.

In one embodiment of this aspect, said composition comprises:
2 mg/mL to 25 mg/mL anakinra;
10 mM-50 mM HEPES buffer; and
15 mg/mL-25 mg/mL taurine.

In one embodiment of this aspect, said composition comprises:
2 mg/mL to 25 mg/mL anakinra;
10 mM-50 mM HEPES buffer; and
20 mg/mL-30 mg/mL hydroxyproline.

In one embodiment of this aspect, said composition comprises:
2 mg/mL to 25 mg/mL anakinra;
10 mM-50 mM HEPES buffer;
10 mg/mL-15 mg/mL taurine; and
10 mg/mL-15 mg/mL hydroxyproline.

Compositions as defined above have been subjected to stability tests and have in such tests displayed good properties.

In one embodiment of this aspect, said buffer is a mixture of 10 mM HEPES buffer and 1.2 mM sodium citrate buffer. Said buffer mixture may furthermore stabilize the pH of the composition at about 6.5.

In one embodiment of this aspect, said at least one osmolyte represents taurine. In particular, said at least one osmolyte represents 20 mg/mL to 40 mg/mL taurine.

In one embodiment of this aspect, said composition comprises:
5 mg/mL to 25 mg/mL anakinra;
10 mM HEPES buffer, which stabilizes the pH of the composition at about 6.5;
0.5 mM EDTA;
0.1% polysorbate 80;
1 mg/mL to 1.5 mg/mL NaCl; and
30 mg/mL taurine.

In one embodiment of this aspect, said composition comprises:
5 mg/mL to 25 mg/mL anakinra;
a mixture of 10 mM HEPES and 1.2 mM sodium citrate buffer, which stabilizes the pH of the composition at about 6.5;
0.5 mM EDTA;
0.1% polysorbate 80;
1 mg/mL to 1.5 mg/mL NaCl; and
30 mg/mL taurine.

In one embodiment of this aspect, said composition comprises:
5 mg/mL to 25 mg/mL anakinra;
10 mM HEPES buffer, which stabilizes the pH of the composition at about 6.5; and
about 30 mg/mL taurine.

In one embodiment of this aspect, said composition comprises:
5 mg/mL to 25 mg/mL anakinra;
10 mM HEPES buffer, which stabilizes the pH of the composition at about 6.5; and
about 30 mg/mL hydroxyproline.

In one embodiment of this aspect, said composition comprises:
5 mg/mL to 25 mg/mL anakinra;
10 mM HEPES buffer, which stabilizes the pH of the composition at about 6.5;
0.5 mM EDTA;
0.1% Polysorbate 80;
1 mg/mL to 1.5 mg/mL NaCl; and
about 30 mg/mL taurine.

In one embodiment of this aspect, said composition comprises from about 15 mg/mL to about 25 mg/mL anakinra.

In one embodiment of this aspect, said composition comprises
5 mg/mL to 25 mg/mL anakinra;
a mixture of 10 mM HEPES and 1.2 mM sodium citrate buffer, which stabilizes the pH of the composition at about 6.5;
0.5 mM EDTA;
0.1% polysorbate 80;
1 mg/mL to 1.5 mg/mL NaCl; and
30 mg/mL taurine.

In one embodiment, the composition according to aspects disclosed herein, is free or essentially free of citrate.

In one embodiment, the composition according to aspects disclosed herein is administered topically to a subject, for example a human or other mammal. Topical administration for example includes ocular administration, i.e. administration to the eye; dermal or mucosal administration.

In one aspect of the present invention, the compositions are administered topically to the eye.

Topical ophthalmic drugs are generally self-administered by patients. Since the patient may be storing a drug for a relatively long period of time and for convenience also need to be able to handle the drug for some time at ambient temperature, the formulation may be subjected to higher temperatures and greater levels of agitation stress than a formulation that is typically stored only by a physician or pharmacist prior to administration or alternatively for a patient handling a temperature sensitive drug only aimed at medication in the patient's home. As is known in the art, proteins are more sensitive to agitation and elevated temperature than small molecules. Agitation stress can lead to precipitation and heat stress can lead to precipitation and to chemical degradation. In addition, during loading of a compound into a delivery device, there can be exposure to heat stress.

The compositions of the present invention are useful in the treatment of topical disorders such as ophthalmic disorders, IL-1 related disorders, inflammatory ocular disorders, and in particular ophthalmic IL-1 related disorders.

IL-1 related disorders include primary or secondary Sjögren's syndrome, such as keratokonjunctivitis sicca associated with Sjögren's syndrome, Non-Sjögren's syndrome, such as lacrimal gland disease or lacrimal duct obstruction; dry eye disorders, keratitis sicca, sicca syndrome, xerophthalmia, tear film disorder, decreased tear production, aqueous tear deficiency, dry eye associated with graft-versus-host disease and Meibomian gland dysfunction.

Disorders also include corneal ocular surface inflammatory conditions, corneal neovascularization, keratitis, incuding peripheral ulcerative keratitis and microbial keratitis;

corneal wound healing, corneal transplantation/keratoplasty, keratoprosthesis surgery, lamellar transplantation, selective endothelial transplantation.

Disorders also include disorders affecting the conjunctiva such as conjunctival scarring disorders and conjunctivitis, for example allergic conjunctivitis and severe allergic conjunctivitis, pemphigoid syndrome and Stevens-Johnson syndrome.

Disorders also include allergic reactions affecting the eye, such as severe allergic (atopic) eye disease also known as allergic conjunctivitis.

Disorders also include autoimmune disorders affecting the eye, such as sympathetic ophthalmia, Vogt-Koyanagi Harada (VKH) syndrome, birdshot retinochoriodopathy, ocular cicatricial pemphigoid, Fuch's heterochronic iridocyclitis and various forms of uveitis.

Disorders also include diabetic retinopathy, diabetic macular edema, uveitis, thyroid eye disease, ectropion/entropion, contact lens allergy and dry eye disease.

Consequently, in one aspect of the invention, there is provided a pharmaceutical composition for use in treatment of an ophtalmic disorder. Pharmaceutical compositions of the invention can be formulated in a variety of forms, such as eye drops, suspensions and ointments.

In one embodiment of this aspect, said ophthalmic disorder is an inflammatory ocular disorder.

In one embodiment of this aspect, said ophthalmic disorder is an IL-1 related disorder.

In one embodiment of this aspect, said ophthalmic disorder is an ophthalmic IL-1 related disorder.

In one embodiment of this aspect, said ophthalmic disorder is selected from primary or secondary Sjögren's syndrome, such as keratokonjunctivitis sicca associated with Sjögren's syndrome, Non-Sjögren's syndrome, such as lacrimal gland disease or lacrimal duct obstruction; dry eye disorders, keratitis sicca, sicca syndrome, xerophthalmia, tear film disorder, decreased tear production, aqueous tear deficiency, dry eye associated with graft-versus-host disease, Meibomian gland dysfunction, corneal ocular surface inflammatory conditions, corneal neovascularization, keratitis, incuding peripheral ulcerative keratitis, microbial keratitis, corneal wound healing, corneal transplantation/keratoplasty, keratoprosthesis surgery, lamellar transplantation, selective endothelial transplantation, conjunctival scarring disorders, conjunctivitis, for example allergic conjunctivitis and severe allergic conjunctivitis, pemphigoid syndrome and Stevens-Johnson syndrome, allergic reactions affecting the eye, such as severe allergic (atopic) eye disease also known as allergic concjunctivitis, autoimmune disorders affecting the eye, such as sympathetic ophthalmia, Vogt-Koyanagi Harada (VKH) syndrome, birdshot retinochoriodopathy, ocular cicatricial pemphigoid, Fuch's heterochronic iridocyclitis and various forms of uveitis, diabetic retinopathy, diabetic macular edema, thyroid eye disease, ectropion/entropion, contact lens allergy and dry eye disease.

In one embodiment of this aspect, said ophthalmic disorder is selected from primary or secondary Sjögren's syndrome, Non-Sjögren's syndrome; dry eye disorder, keratitis sicca, sicca syndrome, xerophthalmia, tear film disorder, decreased tear production, aqueous tear deficiency, dry eye associated with graft-versus-host disease, Meibomian gland dysfunction, corneal ocular surface inflammatory conditions, corneal neovascularization, keratitis, corneal wound healing, corneal transplantation/keratoplasty, keratoprosthesis surgery, lamellar transplantation, selective endothelial transplantation, conjunctival scarring disorders, allergic conjunctivitis, pemphigoid syndrome, Stevens-Johnson syndrome, sympathetic ophthalmia, Vogt-Koyanagi Harada (VKH) syndrome, birdshot retinochoriodopathy, ocular cicatricial pemphigoid, Fuch's heterochronic iridocyclitis, diabetic retinopathy, diabetic macular edema, thyroid eye disease, ectropion/entropion, contact lens allergy and dry eye disease.

In one embodiment of this aspect, said ophthalmic disorder is allergic conjunctivitis.

In one aspect of the invention, there is provided use of a pharmaceutical composition in the preparation of a medicament useful in treatment of an ophtalmic disorder.

In one embodiment of this use aspect, said ophthalmic disorder is an inflammatory ocular disorder.

In one embodiment of the use aspect, said ophthalmic disorder is an IL-1 related disorder.

In one embodiment of the use aspect, said ophthalmic disorder is an ophthalmic IL-1 related disorder.

In one embodiment of the use aspect, said ophthalmic disorder is selected from an ophthalmic disorder as defined in other aspects herein.

In one aspect of the invention, there is provided a method for treating an ophthalmic disorder, comprising administering a therapeutically effctive amount of a pharmaceutical composition of the invention to a subject in need thereof. Typically, said subject is a mammal, such as a human.

In one embodiment of this aspect, said ophthalmic disorder is an inflammatory ocular disorder.

In one embodiment of this aspect, said ophthalmic disorder is allergic conjunctivitis.

In one embodiment of this aspect, said ophthalmic disorder is an IL-1 related disorder.

In one embodiment of this aspect, said ophthalmic disorder is an ophthalmic IL-1 related disorder.

In one embodiment of this aspect, said ophthalmic disorder is selected from an ophthalmic disorder as defined in other aspects herein.

In one embodiment of this aspect, said pharmaceutical composition is administered topically. In particular, said pharmaceutical composition is administered topically to the eye of the subject.

Some manufacturing or filling processes require at least brief exposure of a composition to a relatively high temperature. Thus, for manufacturing purposes it is often required that a composition is temperature stable, e.g. such that it can withstand the conditions required for the manufacturing and dispensation of the composition in a container.

In one aspect of the present invention, there is provided a drug delivery device comprising a composition as defined herein.

In one embodiment, said drug delivery device is a multi use container or a single use container.

By "single or multi use container" is meant a container which holds the composition and is designed to deliver one or several doses at one specific occasion (single use container) or deliver several doses at multiple occasions (multi use container). Multi use containers of sterile drugs typically contain compositions including one or more preservatives, in order to allow for opening the container for withdrawing the various doses under several days, still maintaining the microbiological safety of the composition.

In one embodiment, the composition of the invention is provided in a blow-fill-seal container.

By "blow fill seal container" is meant a container made of a polymeric material which is formed, filled, and sealed in a continuous process without human intervention, in a sterile enclosed area inside a machine. The technology can be used to aseptically manufacture sterile pharmaceutical liquid dosage forms. For example, loading a formulation into a blow fill seal (BFS) container can result in exposure of the formulation to elevated temperatures, in addition to agitation and/or mechanical stress associated with the filling process.

The composition as disclosed herein preferably exhibits improved stability under particular conditions. Stability of the composition may for example be assessed by using one or more methods described herein, such as assessment of visual appearance; UV spectroscopy; size exclusion HPLC (SE-HPLC); reverse phase HPLC (RP-HPLC); cation exchange HPLC (CE-HPLC); turbidity; a light obscuration particle count test; a microscopic particle count test Or level of monomer content. When stability assessments are made based on visual appearance, the composition's opalescence, color, and content of particulates is for example evaluated. The skilled person is aware of other methods for assessing stability of a composition.

In one embodiment relevant to the various aspects of the invention as disclosed herein, the composition is stable after storage for a period of at least one week, at least two weeks, at least three weeks, at least four weeks, at least five weeks or at least six weeks or longer, such as 3, 4, 5 or 6 months, under ambient conditions.

In one embodiment, the composition is stable at a temperature of about 20° C. to about 40° C., for example at a temperature of about 25° C. to about 35° C., such as at a temperature of about 30° C., for a time period of at least two days; three days; five days; one week; ten days; two weeks; three weeks; four weeks; five weeks, or six weeks.

In one embodiment, the composition is stable at a temperature of about 2° C. to about 15° C., for example at a temperature of about 2° C. to about 8° C., for a time period of at least one week; two weeks; three weeks; four weeks; five weeks; six weeks; eight weeks, 16 weeks, 20 weeks, 25 weeks, 30 weeks, 35 weeks, 40 weeks, 45 weeks, one month, two months, three months, four months, five months, six months, seven months, eight months, or more, such as 1 to 5 years.

EXAMPLES

General Material and Methods

The following materials and methods were used in the Examples below. Anakinra stock solution: 220 mg/mL anakinra in CSE (i.e. citrate, salt, EDTA) buffer: 10 mM sodium citrate, 140 mM sodium chloride, 0.5 mM EDTA, pH 6.5.

HPLC methods were set up according to in-house standard protocols. For size exclusion chromatography (SE-HPLC) analyses, a TSK-Gel G2000 SWXL 7.8 mm×30 cm column was used. The mobile phase was CSE Buffer, the injection volume/concentration was 100 μL/5 mg/mL, the wavelength was 280 nm, and the flow rate was 0.5 mL/min.

For cation-exchange high-pressure liquid chromatography (CE-HPLC) analyses a Tosoh SPSPW Protein Pak 7.5 mm×7.5 cm column was used, mobile phase A was 20 mM MES, pH 5.5, and mobile phase B was 20 mM MES, 1 M NaCl, pH 5.5. The injection volume/concentration was 100 μL/5 mg/mL, the wavelength was 280 nm, and the flow rate was 0.5 mL/min.

For reversed-phase high-pressure liquid chromatography analyses, Phenomenex Jupiter C4 RP 250×4.6 mm column was used. Mobile phase A was 0.1% TFA in water and mobile phase B was 0.1% TFA in 90% Acetonitrile. The injection volume/concentration was 50 μL/0.3 mg/mL, the wavelength was 215 nm, and the flow rate was 1 mL/min.

Visual observations were made on the compositions by means of inspecting the solution in a circular glass container, against a black and white background. Opalescence (turbidity) and visual particulates were noted.

The turbidity of compositions was quantified using a HACH 2100AN Turbidimeter. Turbidimeter values are quoted in nephelometric turbidity units (NTU) where a numerical value represents degree of turbidity or opalescence of a solution.

Example 1

Stability of Osmolyte Compositions at 35° C.

Anakinra stock solution was diluted to 30 mg/mL anakinra in osmolyte compositions with or without NaCl. Eleven different osmolytes were tested as follows:
- (a) Anakinra stock solution diluted with aqueous solutions of osmolytes in deionised water, compositions 1-11. Concentrations of NaCl, citrate and EDTA after dilution of the stock solution of anakinra in CSE buffer with the aqueous osmolyte solutions: NaCl=19.1 mM (1.12 mg/ml); citrate=1.36 mM; EDTA=0.07 mM, and
- (b) Anakinra stock solution diluted with aqueous solutions of osmolytes in 19.2 mM NaCl, compositions 12-22. Concentrations of NaCl, citrate and EDTA after dilution of the stock solution of anakinra in CSE buffer with the aqueous NaCl-osmolyte solutions: NaCl=38.2 mM (2.24 mg/ml); citrate=1.36 mM; EDTA=0.07 mM.

The compositions (22 in all) were adjusted to pH 6.5+/− 0.1, stored at 35° C. and monitored over 2 weeks.

TABLE 1

Compositions of anakinra (30 mg/mL) diluted with osmolyte solutions. All compositions contain 1.36 mM citrate buffer and 0.07 mM EDTA.

| Exp. | Osmolyte | Diluent composition | Concentration of osmolyte (mg/mL) | Concentration of NaCl (mg/mL) |
| --- | --- | --- | --- | --- |
| 01 | L-proline | $H_2O$ | 30.13 | 1.12 |
| 02 | D-threonine | $H_2O$ | 31.17 | 1.12 |
| 03 | L-serine | $H_2O$ | 27.51 | 1.12 |
| 04 | myoinositol | $H_2O$ | 47.15 | 1.12 |
| 05 | maltitol | $H_2O$ | 90.11 | 1.12 |
| 06 | D-raffinose pentahydrate | $H_2O$ | 155.76 | 1.12 |
| 07 | hydroxyproline | $H_2O$ | 34.32 | 1.12 |
| 08 | taurine | $H_2O$ | 32.79 | 1.12 |
| 09 | glycine betaine | $H_2O$ | 30.65 | 1.12 |
| 10 | sucrose | $H_2O$ | 89.58 | 1.12 |
| 11 | mannitol | $H_2O$ | 47.68 | 1.12 |
| 12 | L-proline | 1.12 mg/mL NaCl | 25.56 | 2.24 |
| 13 | D-threonine | 1.12 mg/mL NaCl | 26.44 | 2.24 |
| 14 | L-serine | 1.12 mg/mL NaCl | 23.33 | 2.24 |
| 15 | myoinositol | 1.12 mg/mL NaCl | 40.00 | 2.24 |
| 16 | maltitol | 1.12 mg/mL NaCl | 76.44 | 2.24 |
| 17 | D-raffinose pentahydrate | 1.12 mg/mL NaCl | 131.98 | 2.24 |
| 18 | hydroxyproline | 1.12 mg/mL NaCl | 29.11 | 2.24 |
| 19 | taurine | 1.12 mg/mL NaCl | 27.78 | 2.24 |
| 20 | glycine betaine | 1.12 mg/mL NaCl | 26.00 | 2.24 |

TABLE 1-continued

Compositions of anakinra (30 mg/mL) diluted with osmolyte solutions. All compositions contain 1.36 mM citrate buffer and 0.07 mM EDTA.

| Exp. | Osmolyte | Diluent composition | Concentration of osmolyte (mg/mL) | Concentration of NaCl (mg/mL) |
|---|---|---|---|---|
| 21 | sucrose | 1.12 mg/mL NaCl | 75.99 | 2.24 |
| 22 | mannitol | 1.12 mg/mL NaCl | 40.44 | 2.24 |

Minimal changes were observed both in terms of monomer content by SE-HPLC and measured turbidity over the 2 week analysis period, however, the compositions containing NaCl were visually clearer than those prepared with deionised water.

Four osmolyte compositions provided improvements based on visual appearance, with optically clear and minimum particulate content after 2 weeks at 35° C.:
12 (proline+NaCl),
18 (hydroxyproline+NaCl),
19 (taurine+NaCl) and
22 (mannitol+NaCl.

These four compositions were visually clearer compared to the other compositions showing that these four osmolytes provided a stabilizing effect on anakinra.

Example 2

Formulation of Anakinra in Various Buffers

Formulation in HEPES Buffer
Anakinra stock solution was diluted to 60 mg/mL protein in CSE buffer and dialysed into 10 mM HEPES, 38.2 mM NaCl, pH 6.3, 6.5 and 6.9. In all cases, 10 mL protein solution was dialysed against 2×2 L of buffer.

After dialysis, compositions were further diluted to 30 mg/mL anakinra with 10 mM HEPES buffer containing various osmolytes and 38.2 mM NaCl such that the compositions would be isotonic at a target of 280-320 mOsm/kg. Altogether, 12 compositions were prepared (4 osmolytes at pH 6.3, 6.5 and 6.9, respectively) and stored at 35° C., with full analysis at t=0, 2, 4 and 8 weeks. As a reference anakinra 30 mg/mL in CSE was used. This composition has been stored and tested under identical conditions as the other compositions.

Measured concentration by 280 nm UV indicated no loss of protein over the 8 week analysis period. Upon storage there was a reduction in monomer content for all samples as measured by SE-HPLC. The anakinra monomer content measured by SE-HPLC after 4 weeks was significantly higher in HEPES buffer compared to in CSE buffer (>99.0% vs 97.9%).

It was identified that turbidity after 2 weeks storage at 35° C. was generally better for anakinra formulated in HEPES buffer than anakinra formulated in CSE buffer. In comparison, the turbidity of a 30 mg/mL anakinra solution in CSE buffer at pH 6.5, stored for 2 weeks in 35° C., was 15.6 NTU.

Comparable data for anakinra formulated in HEPES buffer at pH 6.5 with osmolytes was 6-9 NTU after two weeks of storage. For samples at pH 6.3 and 6.9 the turbidity values were in all cases except one (proline, pH 6.3) better than the turbidity of anakinra in CSE buffer at the same pH. For anakinra samples in HEPES buffer at pH 6.5 including proline, hydroxyproline, taurine or mannitol, turbidity was low even after 8 weeks, see Table 2 below.

TABLE 2

Turbidity of anakinra formulated in HEPES buffer including osmolyte.

| | | | Turbidity (NTU) | | | |
|---|---|---|---|---|---|---|
| Exp. | Osmolyte | pH | start | 2 weeks | 4 weeks | 8 weeks |
| 23 | Proline | 6.3 | 3.44 | 21 | 30.9 | 29.2 |
| 24 | Hydroxy-proline | 6.3 | 3.46 | 15 | 29.1 | 48.7 |
| 25 | Taurine | 6.3 | 3.4 | 8.57 | 15.1 | 13.6 |
| 26 | Mannitol | 6.3 | 3.96 | 10.5 | 15.9 | 33.5 |
| 27 | Proline | 6.5 | 2.78 | 6.42 | 12.3 | 15.7 |
| 28 | Hydroxy-proline | 6.5 | 2.88 | 9.22 | 17 | 21.1 |
| 29 | Taurine | 6.5 | 2.75 | 6.11 | 8.82 | 12.9 |
| 30 | Mannitol | 6.5 | 3.36 | 6.4 | 8.13 | 11.7 |
| 31 | Proline | 6.9 | 2.84 | 5.93 | 12.1 | 37.1 |
| 32 | Hydroxy-proline | 6.9 | 2.75 | 5.48 | 9.07 | 27.1 |
| 33 | Taurine | 6.9 | 2.49 | 8.64 | 12.3 | 10.3 |
| 34 | Mannitol | 6.9 | 2.6 | 6.85 | 14.5 | 30.9 |

Formulation of Anakinra in His HCl Buffer
Anakinra stock solution was diluted to 60 mg/mL anakinra in CSE and dialysed into 10 mM His HCl, 38.2 mM NaCl, pH 6.5.

After dialysis, compositions were further diluted to 30 mg/mL anakinra in various osmolyte compositions (taurine, hydroxyproline, proline, mannitol) also containing 10 mM His HCl and 38.2 mM NaCl such that the compositions would be isotonic at a target of 280 mOsm/kg. Compositions were stored at 35° C. and full analysis was carried out at t=0, 2 and 4 weeks.

Measured protein concentration showed no loss of protein content after 4 weeks at 35° C.

The SE-HPLC analysis method showed a reduction in monomer content, however most compositions containing anakinra in His buffer were superior to anakinra in CSE buffer, see Table 3.

TABLE 3

Monomer content of anakinra formulated in His buffer including osmolyte after storage at 35° C.

| | Anakinra | | Monomer anakinra content (% by SE-HPLC) | | |
|---|---|---|---|---|---|
| Exp. | Mg/mL | Osmolyte | Start | 2 weeks | 4 weeks |
| 35 | 30 | Proline | 99.87 | 99.75 | 99.98 |
| 36 | 30 | Hydroxyproline | 99.87 | 99.70 | 99.13 |
| 37 | 30 | Taurine | 99.87 | 99.71 | 99.53 |
| 38 | 30 | Mannitol | 99.87 | 99.65 | 98.13 |

Formulation of Anakinra in Tris HCl Buffer
Anakinra stock solution was diluted to 60 mg/mL anakinra in CSE buffer and dialysed into 10 mM Tris HCl, 38.2 mM NaCl, pH 6.5.

After dialysis, compositions were further diluted to 30 mg/mL anakinra in various osmolyte compositions also containing 10 mM Tris HCl and 38.2 mM NaCl such that the compositions would be isotonic at a target of 280 mOsm/kg. Compositions were stored at 35° C. and full analysis was carried out at t=0, 2 and 4 weeks.

Similarly, the compositions showed no loss of protein content upon measurement of protein concentration after 4 weeks at 35° C. SE-HPLC showed a slight decrease in monomer content upon storage at 35° C. but the decrease was generally less than for anakinra in CSE buffer, see Table 4.

TABLE 4

Monomer content of anakinra formulated in Tris buffer including osmolyte after storage at 35° C.

| Anakinra | | | Monomer anakinra content (% by SE-HPLC) | | |
|---|---|---|---|---|---|
| Exp. | Mg/mL | Osmolyte | Start | 2 weeks | 4 weeks |
| 39 | 30 | Proline, | 99.87 | 99.74 | 98.34 |
| 40 | 30 | Hydroxyproline | 99.87 | 99.72 | 99.44 |
| 41 | 30 | Taurine | 99.87 | 99.68 | 99.26 |
| 42 | 30 | Mannitol | 99.87 | 99.65 | 99.22 |

Conclusion

A comparison of the stability of anakinra 30 mg/mL in CSE, HEPES, His and Tris buffer shows that the stability after 4 weeks is better in HEPES, His and Tris buffers than in CSE. The overall conclusion is that HEPES buffer provides optimal stability of anakinra and that this applies also in the presence of an osmolyte. These compositions based on HEPES buffer gave the best overall stability profile when all analytic methods (protein concentration, SE-HPLC and turbidity) were taken into consideration.

Example 3

Compositions, Comprising Anakinra in HEPES Buffer, and at Least One Osmolytic Agent Preparation Frozen anakinra stock solution was thawed and dialysed against 10 mM HEPES, NaCl (2.24 mg/mL), EDTA (0.5 mM), polysorbate 80 (PS80: 1 mg/mL), at a pH of 6.5 together with various osmolytes. All samples were dialysed on a 2×12.5 mL scale against 2×2000 mL buffer. Following dialysis the solution was aliquoted and diluted with stock composition of osmolytes/NaCl/EDTA/PS80. The concentrations of the osmolytes were varied to obtain isotonicity (280-320 mOsmol/kg) in the final compositions. The obtained compositions are set out in Table 5.

The diluted material was stored in glass tubes at 30° C. and evaluated visually for turbidity at regular intervals during 2 weeks storage. The results are presented in Table 5.

TABLE 5

Turbidity of anakinra compositions in HEPES buffer, 0.19 mg/ml EDTA, 1 mg/ml PS80 and other components as defined below.

| | Anakinra | | NaCl | | Turbidity (NTU) | | | | |
|---|---|---|---|---|---|---|---|---|---|
| Exp. | mg/mL | Buffer | mg/mL | Osmolyte | Start | 2 days | 5 days | 7 days | 14 days |
| 43 | 25 | HEPES 10 mM | 2.24 | Proline 22.1 mg/mL | 4.12 | 4.64 | 5.94 | 7.44 | 10.8 |
| 44 | 25 | HEPES 10 mM | 2.24 | Hydroxyproline 25.2 mg/mL | 2.29 | 11.6 | 15.6 | 18.7 | 18.5 |
| 45 | 25 | HEPES 10 mM | 2.24 | Taurine 24.0 mg/mL | 2.25 | 3.36 | 4.84 | 6.37 | 7.93 |
| 46 | 25 | HEPES 10 mM | 2.24 | Mannitol 35.0 mg/mL | 2.78 | 3.9 | 5.78 | 6.48 | 10.1 |
| 47 | 10 | HEPES 10 mM | 2.24 | Proline 22.1 mg/mL | 1.34 | 2.88 | 3.74 | 5.53 | 7.1 |
| 48 | 10 | HEPES 10 mM | 2.24 | Hydroxyproline 25.2 mg/mL | 1.48 | 10.3 | 15.2 | 19 | 19 |
| 49 | 10 | HEPES 10 mM | 2.24 | Taurine 24.0 mg/mL | 1.39 | 2.69 | 4.07 | 4.26 | 5.54 |
| 50 | 10 | HEPES 10 mM | 2.24 | Mannitol 35.0 mg/mL | 1.85 | 3.47 | 5.09 | 5.83 | 7.73 |
| 51 | 2 | HEPES 10 mM | 2.24 | Proline 22.1 mg/mL | 1.2 | 3.69 | 4.53 | 4.73 | 7.2 |
| 52 | 2 | HEPES 10 mM | 2.24 | Hydroxyproline 25.2 mg/mL | 0.69 | 15.6 | 20.4 | 21.4 | 22.2 |
| 53 | 2 | HEPES 10 mM | 2.24 | Taurine 24.0 mg/mL | 0.99 | 1.93 | 3.05 | 3.49 | 4.22 |
| 54 | 2 | HEPES 10 mM | 2.24 | Mannitol 35.0 mg/mL | 0.96 | 4 | 5.72 | 6.42 | 9.47 |

As can be seen in the Table 5, anakinra compositions in HEPES buffer comprising the osmolytes taurine, proline and mannitol displayed best results in terms of turbidity after 14 days of storage. Compositions including the osmolyte taurine showed superior results than compositions including any of the other osmolytes.

Example 4

Compositions, Comprising Anakinra in Citrate Buffer, and at Least One Osmolyte

Preparation

Frozen anakinra stock solution was thawed and diluted with 10 mM sodium citrate, 2.24 mg/mL NaCl, 0.5 mM EDTA, polysorbate 80 1 mg/mL, pH 6.5 and various osmolytes. The concentration of the osmolytes was varied to obtain isotonic compositions (about 300 mOsmol/kg). The dilution resulted in compositions as disclosed in Table 6 below.

The diluted material was stored in glass tubes at 30° C. and analyzed at regular intervals during 8 weeks storage.

TABLE 6

Turbidity of anakinra compositions in 10 mM sodium citrate buffer, 1 mg/ml PS80, 2.24 mg/ml NaCl, 0.19 mg/ml EDTA and the components defined below.

| | Anakinra | | Turbidity (NTU) | | | |
|---|---|---|---|---|---|---|
| Exp. | mg/mL | Osmolyte | Start | 2 weeks | 4 weeks | 8 weeks |
| 55 | 25 | Proline, 22.1 mg/mL | 1.75 | 3.89 | 4.51 | 6.5 |
| 56 | 25 | Hydroxyproline 25.2 mg/mL | 1.85 | 4.33 | 4.4 | 6.49 |
| 57 | 25 | Taurine 24.0 mg/mL | 1.72 | 3.44 | 4.83 | 5.54 |
| 58 | 25 | Mannitol 35.0 mg/mL | 1.76 | 4.26 | 4.21 | 5.49 |
| 59 | 25 | Myoinositol 34.6 mg/mL | 1.9 | 5.75 | 6.75 | 7.89 |
| 60 | 25 | Methionine 28.6 mg/mL | 1.72 | 3.53 | 3.55 | 5.8 |
| 61 | 25 | Sucrose 66.7 mg/mL | 1.69 | 5.36 | 7.16 | 39.1 |
| 62 | 15 | Proline, 22.1 mg/mL | 1.35 | 2.97 | 3.37 | 4.74 |
| 63 | 15 | Hydroxyproline 25.2 mg/mL | 1.23 | 3.82 | 3.74 | 5.66 |
| 64 | 15 | Taurine 24.0 mg/mL | 1.26 | 1.69 | 3.21 | 4.18 |
| 65 | 15 | Mannitol 35.0 mg/mL | 1.24 | 3.55 | 3.5 | 3.52 |
| 66 | 15 | Myoinositol 34.6 mg/mL | 1.9 | 4.36 | 5.42 | 7.09 |
| 67 | 15 | Methionine 28.6 mg/mL | 1.36 | 3.28 | 3.51 | 4.86 |
| 68 | 15 | Sucrose 66.7 mg/mL | 1.56 | 4.41 | 7.42 | 21.6 |
| 69 | 2 | Proline, 22.1 mg/mL | 0.629 | 2.98 | 3.17 | 3.27 |
| 70 | 2 | Hydroxyproline 25.2 mg/mL | 0.74 | 2.62 | 4.04 | 3.98 |
| 71 | 2 | Taurine 24.0 mg/mL | 0.588 | 1.12 | 1.69 | 2.81 |
| 72 | 2 | Mannitol 35.0 mg/mL | 0.625 | 2.35 | 3.62 | 3.84 |
| 73 | 2 | Myoinositol 34.6 mg/mL | 0.616 | 3.71 | 4.01 | 5.38 |
| 74 | 2 | Methionine 28.6 mg/mL | 0.627 | 0.914 | 2.88 | 2.82 |
| 75 | 2 | Sucrose 66.7 mg/mL | 0.682 | 3.38 | 5.81 | 14.1 |

For anakinra compositions comprising citrate buffer, selected osmolytes provided some stabilizing effect, depending on the specific osmolyte and relative to each other and most notably at low protein concentration. The selected osmolytes are taurine, mannitol, proline, methionine and hydroxyproline. Osmolytes such as myoinositol or sucrose provided no stabilizing effect.

Example 5

Compositions, Comprising Anakinra in a Mixture of HEPES Buffer and Citrate Buffer, and at Least One Osmolyte Preparation Anakinra stock solution was diluted to anakinra concentrations of 2, 15 and 25 mg/mL with a solution consisting of 10 mM HEPES, 2.24 mg/mL NaCl, 0.5 mM EDTA, polysorbate 80 1 mg/mL, pH 6.5 and various osmolytes. The concentration of the osmolytes was varied to obtain isotonic compositions (300 mOsmol/kg). The resulting compositions contained residuals of sodium citrate at 0.1, 0.7 and 1.1 mM, respectively for the 25, 15 and 2 mg/mL anakinra concentrations. The dilution resulted in the compositions presented in Table 7.

The diluted material was stored in glass tubes at 30° C. and analyzed at regular intervals during 8 weeks storage.

TABLE 7

Turbidity of anakinra compositions comprising 2.24 mg/ml NaCl, 0.19 mg/ml EDTA, 1 mg/ml PS80 and the components defined below.

| | Anakinra | | | Turbidity (NTU) | | | |
|---|---|---|---|---|---|---|---|
| Exp. | Mg/mL | Buffer | Osmolyte | Start | 2 weeks | 4 weeks | 8 weeks |
| 76 | 25 | 10 mM HEPES + 1.1 mM citrate | Proline 22.1 mg/mL | 1.88 | 3.98 | 5.53 | 8.57 |
| 77 | 25 | | Hydroxyproline 25.2 mg/mL | 2 | 2.68 | 4.29 | 5.53 |
| 78 | 25 | | Taurine 24.0 mg/mL | 1.91 | 4.23 | 5.41 | 7.31 |
| 79 | 25 | | Mannitol 35.0 mg/mL | 1.94 | 3.74 | 4.79 | 4.93 |
| 80 | 25 | | Myoinositol 34.6 mg/mL | 2.22 | 6.77 | 8.3 | 13.2 |

TABLE 7-continued

Turbidity of anakinra compositions comprising 2.24 mg/ml NaCl,
0.19 mg/ml EDTA, 1 mg/ml PS80 and the components defined below.

| Anakinra | | | Turbidity (NTU) | | | |
|---|---|---|---|---|---|---|
| Exp. | Mg/mL | Buffer | Osmolyte | Start | 2 weeks | 4 weeks | 8 weeks |

| Exp. | Mg/mL | Buffer | Osmolyte | Start | 2 weeks | 4 weeks | 8 weeks |
|---|---|---|---|---|---|---|---|
| 80 | 25 | | Methionine 28.6 mg/mL | 1.84 | 2.85 | 3.93 | 5.09 |
| 81 | 25 | | Sucrose 66.7 mg/mL | 2.01 | 4.79 | 8.55 | 28 |
| 82 | 15 | 10 mM HEPES + | Proline 22.1 mg/mL | 1.48 | 2.79 | 4.14 | 5.29 |
| 83 | 15 | 0.7 mM citrate | Hydroxyproline 25.2 mg/mL | 1.35 | 1.93 | 3.36 | 4.41 |
| 84 | 15 | | Taurine 24.0 mg/mL | 1.36 | 1.57 | 2.23 | 4.44 |
| 85 | 15 | | Mannitol 35.0 mg/mL | 1.37 | 1.66 | 1.83 | 2.54 |
| 86 | 15 | | Myoinositol 34.6 mg/mL | 1.38 | 4.64 | 4.96 | 16.5 |
| 87 | 15 | | Methionine 28.6 mg/mL | 1.22 | 1.47 | 1.33 | 1.34 |
| 88 | 15 | | Sucrose 66.7 mg/mL | 1.37 | 4.75 | 9.99 | 15.3 |
| 89 | 2 | 10 mM HEPES + | Proline 22.1 mg/mL | 0.726 | 0.827 | 2.69 | 3.55 |
| 90 | 2 | 0.1 mM citrate | Hydroxyproline 25.2 mg/mL | 1.22 | 0.873 | 3.25 | 3.45 |
| 91 | 2 | | Taurine 24.0 mg/mL | 0.71 | 0.663 | 0.692 | 1.17 |
| 92 | 2 | | Mannitol 35.0 mg/mL | 0.709 | 0.692 | 1.73 | 2.6 |
| 93 | 2 | | Myoinositol 34.6 mg/mL | 0.732 | 2.07 | 4.57 | 6.85 |
| 94 | 2 | | Methionine 28.6 mg/mL | 0.653 | 0.642 | 1.12 | 0.684 |
| 95 | 2 | | Sucrose 66.7 mg/mL | 0.948 | 0.809 | 2.32 | 10.1 |

The results confirmed the previously observed stabilizing effect of the osmolytes, this time in a combination of HEPES and citrate buffer. The osmolytes proline, hydroxyproline, taurine, mannitol and methionine showed similar effects on the turbidity of 2-25 mg/mL anakinra solutions in HEPES/citrate buffer compositions. Other osmolytes such as sucrose or myoinositol did not provide protection of anakinra as exhibited in the large increase of turbidity upon storage.

Example 6

Tolerability Study

Frozen anakinra stock compositions (in citrate buffer with NaCl and EDTA) were thawed, aliquoted and diluted with stock compositions of HEPES/NaCl/EDTA/PS80 and various osmolytes. The concentrations of the osmolytes were varied to obtain isotonicity (280-320 mOsmol/kg) in the final compositions, except for the hypotonic composition "K" having an osmolality of 200-250 mOsmol/kg. The tested compositions are set out in Table 8.

TABLE 8

Compositions tested for local tolerance

| Test Item | NaCl mg/mL | PS80 mg/mL | Disodium EDTA dihydrate mg/mL | HEPES mM | Na-citrate mM | Anakinra mg/mL | Osmolyte mg/mL |
|---|---|---|---|---|---|---|---|
| A | 2.24 | 1 | 0.19 | 10 | appr. 1 | 0 | Taurine 24.0 |
| B | 2.24 | 1 | 0.19 | 10 | appr. 1 | 0 | Praline 21.1 |

TABLE 8-continued

Compositions tested for local tolerance

| Test Item | NaCl mg/mL | PS80 mg/mL | Disodium EDTA dihydrate mg/mL | HEPES mM | Na-citrate mM | Anakinra mg/mL | Osmolyte mg/mL |
|---|---|---|---|---|---|---|---|
| C | 2.24 | 1 | 0.19 | 10 | appr. 1 | 0 | Hydroxyproline 25.2 |
| D | 2.24 | 1 | 0.19 | 10 | appr. 1 | 0 | Mannitol 35.0 |
| E | 2.24 | 1 | 0.19 | 10 | appr. 1 | 0 | Methionine 28.6 |
| F | 2.24 | 1 | 0.19 | 10 | appr. 1 | 25 | Taurine 24.0 |
| G | 2.24 | 1 | 0.19 | 10 | appr. 1 | 25 | Proline 22.1 |
| H | 2.24 | 1 | 0.19 | 10 | appr. 1 | 25 | Hydroxyproline 25.2 |
| I | 2.24 | 1 | 0.19 | 10 | appr. 1 | 25 | Mannitol 35.0 |
| J | 2.24 | 1 | 0.19 | 10 | appr. 1 | 25 | Methionine 28.6 |
| K | 2.24 | 1 | 0.19 | 10 | appr. 1 | 25 | Taurine 15.0 |

Albino rabbits of NZW New Zealand White strain, any gender, were divided into groups of three (3). Each group was tested with one formulation (Test Item, Table 8). The testing was performed by instillation of 50 μL of the respective formulation into the right eye. The instillations were performed during five (5) days on a daily regime as described below. All instillations were performed over a period of 8 hours during each day.

1st day: five (5) 50 μL instillations in right eyes within 20 min
  2nd day: twice daily 50 μL instillations in right eye
  3rd day: four times daily 50 μL instillations in right eyes
  4th day: six times daily 50 μL instillations in right eyes
  5th day: eight times daily 50 μL instillations in right eyes The study evaluation was performed by daily ocular observations using the Draize scoring system (Draize J H, Woodgard G and Calvery H O. Methods for the study of irritation and toxicity of substances applied topically to the skin and mucous membranes. J. Pharmacol. Exp. Ther. 1944; 82: 377-390). The observations were performed on both eyes.

1st day: Draize scoring system with an ophthalmoscope: on pre-test, just after the first administration, then 0.5 h, 1 h, and 4 h after the last administration 2nd day to 5th day: Draize scoring system with an ophthalmoscope: twice daily before the first and after the last administration of the day.

Results

All compositions were generally well tolerated when instilled onto the eye as summarized in Table 9 below. Observations of redness of the conjunctiva were made on one occasion after the initial instillation in one animal each per composition for compositions with proline, hydroxyproline and mannitol. This redness was transient and not found during repeated instillations. One of the animals instilled with methinone (test item E) showed signs of corneal opacity which most probably represents a corneal trauma which was not treatment related. It is concluded that all the tested compositions can be administered ocularly without any severe intolerance effects. Further, the hypotonic composition "K" having an osmolality of 200-250 mOsmol/kg, provided no aberrant observations.

TABLE 9

Results of local tolerance testing

| Group | Test Item | Osmolyte | anakinra mg/mL | Draize test Aberrant observations (number of observations/number of animals treated) | Comments |
|---|---|---|---|---|---|
| 1 | A | Taurine | 0 | 0/3 | — |
| 2 | B | Proline | 0 | 0/3 | — |
| 3 | C | Hydroxyproline | 0 | 1/3 | Redness of conjunctiva on one occasion |
| 4 | D | Mannitol | 0 | 1/3 | Redness of conjunctiva on one occasion |
| 5 | E | Methionine | 0 | 1/3 | Corneal opacity appearing at day 3 and 5 |
| 7 | G | Taurine | 25 | 0/3 | — |
| 8 | H | Proline | 25 | 1/3 | Redness of conjunctiva on one occasion |

TABLE 9-continued

Results of local tolerance testing

| Group | Test Item | Osmolyte | anakinra mg/mL | Draize test Abberant observations (number of observations/ number of animals treated) | Comments |
|---|---|---|---|---|---|
| 9 | I | Hydroxyproline | 25 | 0/3 | — |
| 10 | J | Mannitol | 25 | 0/3 | — |
| 11 | K | Methinone | 25 | 0/3 | — |
| 13 | M | Hypotonic | 25 | 0/3 | — |

Example 7

Stability of Anakinra in Different HEPES Concentrations with or without Osmolytes at 35° C.

Preparation

Frozen anakinra stock solution was thawed, diluted to 50 mg/mL Anakinra and dialyzed for a total of ~18 hours (overnight) at 2-8° C. against a solution of 10, 25 or 50 mM HEPES, 38.2 mM NaCl at pH 6.5. The resulting solutions were aliquoted and diluted with different HEPES/NaCl/osmolyte solutions to yield the final compositions as described in Table 10 below. The concentration of the osmolytes was varied to obtain isotonic compositions (about 280 mOsmol/kg). These solutions were used for the experiments in Examples 7, 8 and 9 below.

TABLE 10

Final anakinra compositions after dilution with stock solutions. All compositions contained 2.23 mg/mL NaCl and had a pH of 6.5. Taurine and Hydroxyproline concentrations were varied to achieve isotonic solutions, unless otherwise denoted in Table. Samples with 10 mM citrate also contained 0.5 mM EDTA.

| Exp. | Description | Anakinra mg/mL | Buffer | Osmolyte Concentration (mg/mL) |
|---|---|---|---|---|
| 96 | 2 mg/mL Anakinra citrate control | 2 | 10 mM citrate | None |
| 97 | 2 mg/mL Anakinra 10 mM HEPES + taurine | 2 | 10 mM HEPES | 24.65 mg/mL Taurine |
| 98 | 2 mg/mL Anakinra 25 mM HEPES + taurine | 2 | 25 mM HEPES | 22.40 mg/mL Taurine |
| 99 | 2 mg/mL Anakinra 50 mM HEPES + taurine | 2 | 50 mM HEPES | 19.27 mg/mL Taurine |
| 100 | 2 mg/mL Anakinra 10 mM HEPES + hydroxyproline | 2 | 10 mM HEPES | 25.87 mg/mL Hydroxyproline |
| 101 | 2 mg/mL Anakinra 25 mM HEPES + hydroxyproline | 2 | 25 mM HEPES | 23.50 mg/mL Hydroxyproline |
| 102 | 2 mg/mL Anakinra 50 mM HEPES + hydroxyproline | 2 | 50 mM HEPES | 20.22 mg/mL Hydroxyproline |
| 103 | 15 mg/mL Anakinra citrate control | 15 | 10 mM citrate | None |
| 104 | 15 mg/mL Anakinra 10 mM HEPES + taurine | 15 | 10 mM HEPES | 24.65 mg/mL Taurine |
| 105 | 15 mg/mL Anakinra 25 mM HEPES + taurine | 15 | 25 mM HEPES | 22.40 mg/mL Taurine |
| 106 | 15 mg/mL Anakinra 50 mM HEPES + taurine | 15 | 50 mM HEPES | 19.27 mg/mL Taurine |
| 107 | 15 mg/mL Anakinra 10 mM HEPES + hydroxyproline | 15 | 10 mM HEPES | 25.87 mg/mL Hydroxyproline |
| 108 | 15 mg/mL Anakinra 25 mM HEPES hydroxyproline | 15 | 25 mM HEPES | 23.50 mg/mL Hydroxyproline |
| 109 | 15 mg/mL Anakinra 50 mM HEPES + hydroxyproline | 15 | 50 mM HEPES | 20.22 mg/mL Hydroxyproline |
| 110 | 25 mg/mL Anakinra citrate control | 25 | 10 mM citrate | None |
| 111 | 25 mg/mL Anakinra 10 mM HEPES + taurine | 25 | 10 mM HEPES | 24.65 mg/mL Taurine |
| 112 | 25 mg/mL Anakinra 25 mM HEPES + taurine | 25 | 25 mM HEPES | 22.40 mg/mL Taurine |
| 113 | 25 mg/mL Anakinra 50 mM HEPES + taurine | 25 | 50 mM HEPES | 19.27 mg/mL Taurine |
| 114 | 25 mg/mL Anakinra 10 mM HEPES + hydroxyproline | 25 | 10 mM HEPES | 25.87 mg/mL Hydroxyproline |
| 115 | 25 mg/mL Anakinra 25 mM HEPES + hydroxyproline | 25 | 25 mM HEPES | 23.50 mg/mL Hydroxyproline |
| 116 | 25 mg/mL Anakinra 50 mM HEPES hydroxyproline | 25 | 50 mM HEPES | 20.22 mg/mL Hydroxyproline |
| 117 | 15 mg/mL Anakinra 10 mM HEPES NaCl | 15 | 10 mM HEPES | None |
| 118 | 15 mg/mL Anakinra 10 mM HEPES osmolyte blend | 15 | 10 mM HEPES | 12.14 mg/mL Taurine/ 12.74 mg/mL Hydroxyproline |

Solutions with 2, 15 and 25 mg/mL anakinra in HEPES buffer of three different concentrations and optionally with one out of two osmolytes were prepared as described in Table 10 above. Control samples at the same anakinra concentrations but formulated in citrate buffer were also prepared. The prepared solutions were stored in glass tubes at 35° C. and analyzed at regular intervals during 8 weeks, by measurement of anakinra monomer content. The analytical results are disclosed in Table 11 and for the protein concentration 25 mg/mL in FIG. 1.

TABLE 11

Monomer content in % determined by SEC-HPLC as described above, in 2, 15 and 25 mg/mL anakinra compositions in 10 mM citrate or HEPES buffers of different concentrations. The citrate buffer also contained 2.24 mg/ml NaCl and 0.19 mg/ml EDTA (0.5 mM). The HEPES samples were optionally formulated with one out of two different osmolytes. Osmolyte concentrations are as set out in Table 10 above.

| | Anakinra | | | Monomer content (%) | | | |
| --- | --- | --- | --- | --- | --- | --- | --- |
| Exp. | (mg/mL) | Buffer | Osmolyte | Start | 2 weeks | 4 weeks | 8 weeks |
| 96 | 2 | 10 mM Citrate | No | 99.67 | 99.52 | 99.49 | 98.76 |
| 97 | 2 | 10 mM HEPES | Taurine | 99.53 | 99.52 | 99.64 | 99.46 |
| 98 | 2 | 25 mM HEPES | Taurine | 97.76 | 99.42 | 99.35 | 99.46 |
| 99 | 2 | 50 mM HEPES | Taurine | 99.34 | 99.27 | 99.29 | 99.32 |
| 100 | 2 | 10 mM HEPES | Hydroxyproline | 99.47 | 99.44 | 99.19 | 99.07 |
| 101 | 2 | 25 mM HEPES | Hydroxyproline | 99.38 | 99.26 | 99.22 | 99.12 |
| 102 | 2 | 50 mM HEPES | Hydroxyproline | 99.56 | 98.60 | 98.40 | 98.69 |
| 103 | 15 | 10 mM Citrate | None | 99.76 | 99.44 | 98.99 | 97.98 |
| 104 | 15 | 10 mM HEPES | Taurine | 99.71 | 99.15 | 99.26 | 98.81 |
| 105 | 15 | 25 mM HEPES | Taurine | 99.73 | 99.57 | 99.30 | 98.86 |
| 106 | 15 | 50 mM HEPES | Taurine | 99.77 | 99.49 | 99.16 | 98.66 |
| 107 | 15 | 10 mM HEPES | Hydroxyproline | 99.75 | 99.52 | 99.40 | 98.88 |
| 108 | 15 | 25 mM HEPES | Hydroxyproline | 99.74 | 99.60 | 99.40 | 99.02 |
| 109 | 15 | 50 mM HEPES | Hydroxyproline | 99.03 | 99.56 | 98.83 | 98.88 |
| 110 | 25 | 10 mM Citrate | None | 99.55 | 99.14 | 98.37 | 96.78 |
| 111 | 25 | 10 mM HEPES | Taurine | 99.67 | 99.18 | 99.07 | 98.21 |
| 112 | 25 | 25 mM HEPES | Taurine | 99.72 | 99.37 | 98.94 | 98.12 |
| 113 | 25 | 50 mM HEPES | Taurine | 99.73 | 99.36 | 99.09 | 98.23 |
| 114 | 25 | 10 mM HEPES | Hydroxyproline | 99.05 | 99.40 | 99.03 | 98.22 |
| 115 | 25 | 25 mM HEPES | Hydroxyproline | 99.73 | 99.44 | 99.17 | 98.40 |
| 116 | 25 | 50 mM HEPES | Hydroxyproline | 99.73 | 99.41 | 99.11 | 98.37 |

TABLE 11-continued

Monomer content in % determined by SEC-HPLC as described above, in 2, 15 and 25 mg/mL anakinra compositions in 10 mM citrate or HEPES buffers of different concentrations. The citrate buffer also contained 2.24 mg/ml NaCl and 0.19 mg/ml EDTA (0.5 mM). The HEPES samples were optionally formulated with one out of two different osmolytes. Osmolyte concentrations are as set out in Table 10 above.

| | Anakinra | | | Monomer content (%) | | | |
|---|---|---|---|---|---|---|---|
| Exp. | (mg/mL) | Buffer | Osmolyte | Start | 2 weeks | 4 weeks | 8 weeks |
| 117 | 15 | HEPES | None | 99.62 | 99.42 | 99.10 | 98.20 |
| 118 | 15 | HEPES | Taurine/ Hydroxyproline | 99.76 | 99.54 | 99.34 | 98.38 |

Conclusions

Figure 1A:
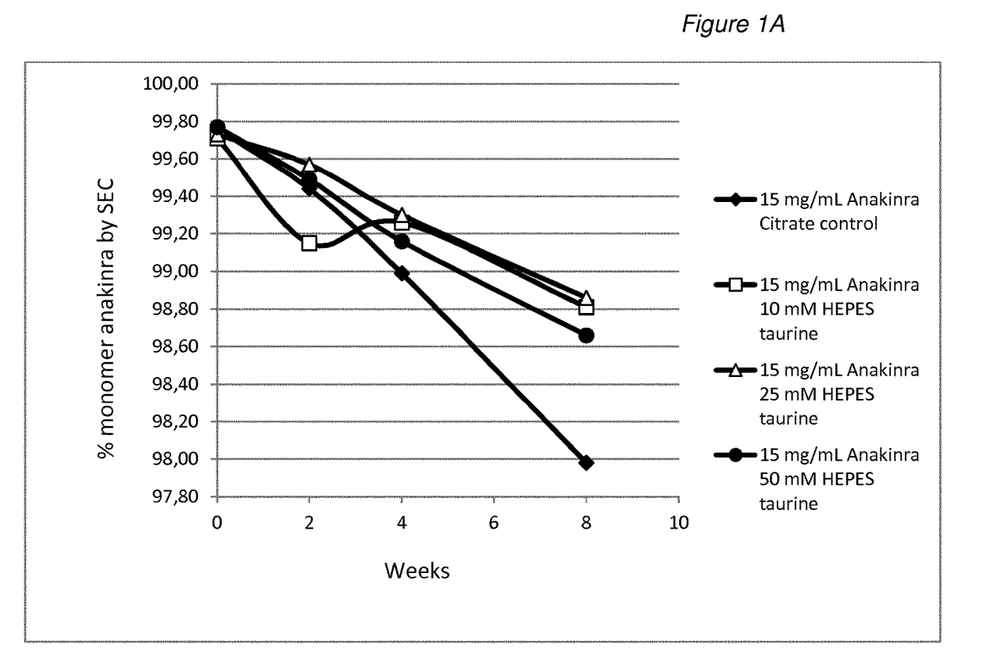
FIG. 1A shows data with the osmolyte taurine being added and FIG. 1B shows data with the osmolyte hydroxyproline being added. Further details are provided in Example 7.
Figure 1B:
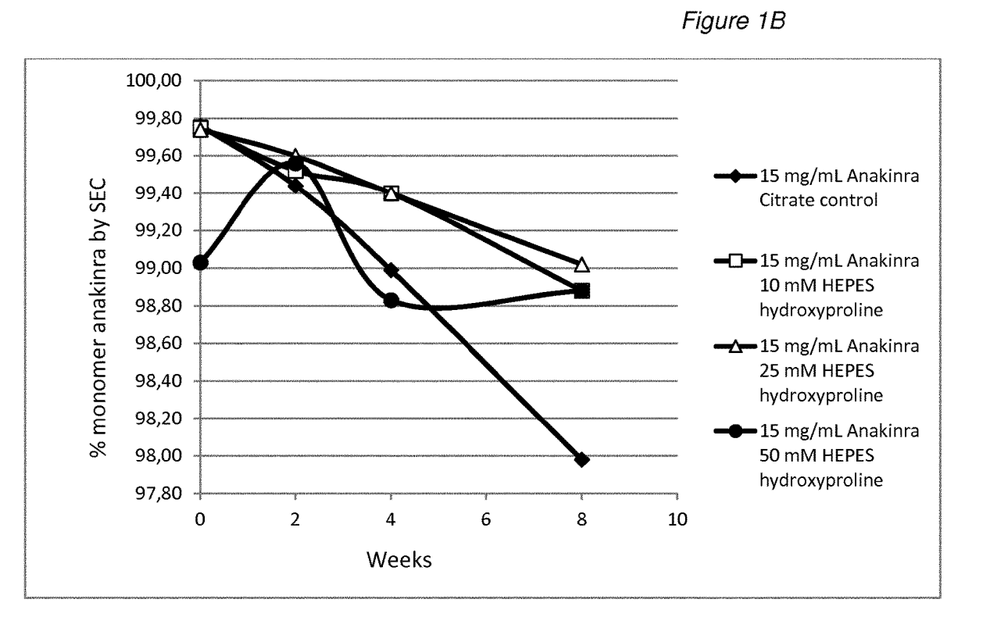

The analytical results in Table 11 and FIG. 1 show that the decrease in monomer content was largest for sample with citrate buffer. The samples with HEPES buffer show a comparatively smaller decrease in monomer content. Varying the HEPES concentration in the range 10 to 50 mM did not affect the stability of anakinra.

Example 8

Stability of Anakinra at Different Concentrations in HEPES with Osmolytes at 35° C.

Preparation

Solutions with 2, 15 and 25 mg/mL anakinra in HEPES buffer and osmolytes were prepared as described in Example 7 and Table 10 above. Control samples at the same anakinra concentrations but formulated in citrate buffer were also prepared.

The prepared solutions were stored in glass tubes at 35° C. and analyzed at regular intervals during 8 weeks. The analytical results are disclosed in Table 12 and for the protein concentration 2, 15 and 25 mg/mL in FIG. 2.

TABLE 12

Monomer content in % of anakinra determined by SEC-HPLC as described above, in anakinra compositions in citrate or HEPES buffers. The 10 mM sodium citrate buffer contained- 2.24 mg/ml NaCl, 0.19 mg/ml EDTA (0.5 mM). The HEPES buffer contained the components defined below. Osmolyte concentrations are as set out in Table 10 above.

| | Anakinra | Buffer | | Monomer content (%) | | | |
|---|---|---|---|---|---|---|---|
| Exp. | (mg/mL) | (10 mM) | Osmolyte | Start | 2 weeks | 4 weeks | 8 weeks |
| 96 | 2 | Citrate | None | 99.67 | 99.52 | 99.49 | 98.76 |
| 97 | 2 | HEPES | Taurine | 99.53 | 99.52 | 99.64 | 99.46 |
| 100 | 2 | HEPES | Hydroxyproline | 99.47 | 99.44 | 99.19 | 99.07 |
| 103 | 15 | Citrate | None | 99.76 | 99.44 | 98.99 | 97.98 |
| 104 | 15 | HEPES | Taurine | 99.71 | 99.15 | 99.26 | 98.81 |
| 107 | 15 | HEPES | Hydroxyproline | 99.75 | 99.52 | 99.40 | 98.88 |
| 110 | 25 | Citrate | None | 99.55 | 99.14 | 98.37 | 96.78 |
| 111 | 25 | HEPES | Taurine | 99.67 | 99.18 | 99.07 | 98.21 |
| 114 | 25 | HEPES | Hydroxyproline | 99.05 | 99.40 | 99.03 | 98.22 |

Conclusions

Figure 2:
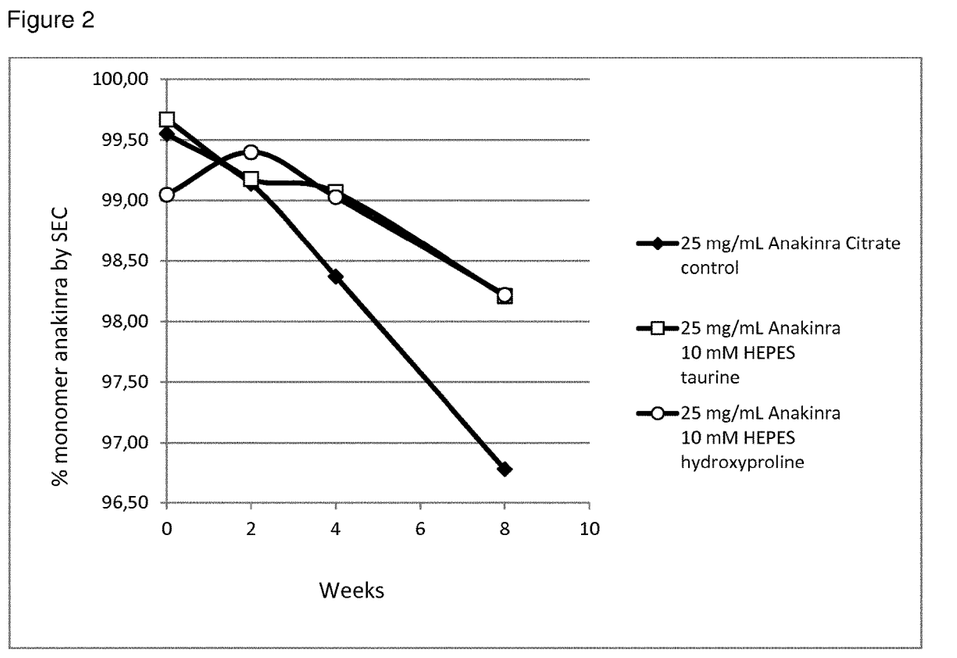
FIG. 2. shows anakinra monomer content in 25 mg/mL anakinra solutions after storage at 35° C. formulated in citrate HEPES or citrate buffers with osmolytes. Further details are provided in Example 8.

The analytical results in Table 12 and FIG. 2 show that the decrease in monomer content was largest for sample with citrate buffer. The samples with HEPES buffer show a comparatively smaller decrease in monomer content than those samples which contained citrate buffer. The two osmolytes taurine or hydroxyproline showed similar stabilizing effects.

Example 9

Stability of Anakinra in HEPES Compositions with or without Osmolytes at 35° C.

Solutions with 15 mg/mL anakinra in HEPES buffer and osmolytes were prepared as described in Example 7 and Table 10 above. Control samples at the same anakinra concentrations but formulated in citrate buffer were also prepared.

The prepared solutions containing anakinra 15 mg/mL formulated in 10 mM HEPES with or without osmolytes or in 10 mM citrate buffer without osmolytes were stored in glass tubes at 35° C. and analyzed at regular intervals during 8 weeks storage. The analytical results are disclosed in Table 13 and FIG. 3.

TABLE 13

Monomer content in % determined by SEC-HPLC as described above, in 15 mg/mL anakinra compositions in 10 mM citrate or HEPES buffers. The citrate buffer also contained 2.24 mg/ml NaCl and 0.19 mg/ml EDTA (0.5 mM). The HEPES samples were formulated with or without osmolytes. Osmolyte concentrations are as set out in Table 10 above.

| | Anakinra | | | Monomer content (%) | | | |
|---|---|---|---|---|---|---|---|
| Exp. | (mg/mL) | Buffer | Osmolyte | Start | 2 weeks | 4 weeks | 8 weeks |
| 103 | 15 | citrate | No | 99.76 | 99.44 | 98.99 | 97.98 |
| 104 | 15 | HEPES | Taurine | 99.71 | 99.15 | 99.26 | 98.81 |
| 107 | 15 | HEPES | Hydroxyproline | 99.75 | 99.52 | 99.40 | 98.88 |
| 117 | 15 | HEPES | No | 99.62 | 99.42 | 99.10 | 98.20 |
| 118 | 15 | HEPES | Taurine/ Hydroxyproline | 99.76 | 99.54 | 99.34 | 98.38 |

Conclusions

Figure 3:
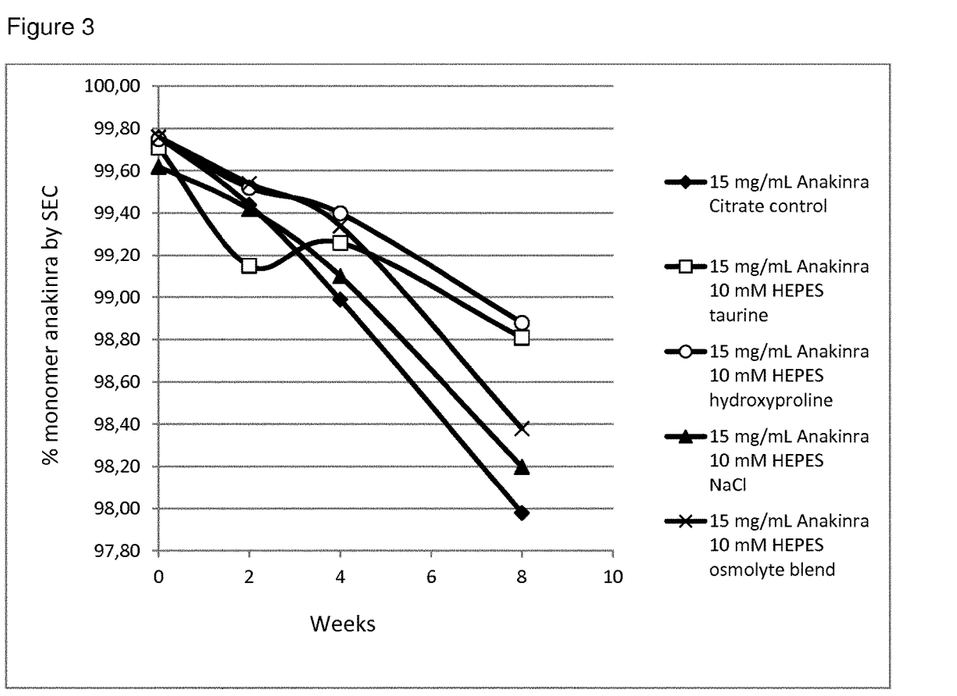
FIG. 3. shows anakinra monomer content in anakinra solutions after storage at 35° C. formulated in HEPES or citrate buffers. Further details are provided in Example 9.

The analytical results in Table 13 and FIG. 3 show that the decrease in monomer content was largest for experiment 103 containing citrate but without HEPES or osmolytes. The other experiments showed a decrease in the order 117, 118>104, 107. For experiments without osmolytes, HEPES buffer generates less anakinra monomer decrease than citrate buffer. In all experiments where HEPES and one or two osmolytes are included, the decrease in monomer content is less than for experiments with HEPES without any osmolyte.

What is claimed is:

1. A liquid pharmaceutical composition for improved stability of anakinra, comprising:
   0.01 mg/mL to 30 mg/mL anakinra;
   5 to 50 mM buffer, selected from HEPES and a mixture of HEPES and sodium citrate, wherein said buffer stabilizes the pH of the composition at pH from 6 to 7;
   1 to 100 mg/mL of at least one osmolyte,
   wherein said at least one osmolyte is selected from taurine, mannitol, proline, and hydroxyproline, and
   0.1 to 5 mg/mL NaCl;
   wherein the composition is stable after storage for a period of at least one week.

2. The liquid pharmaceutical composition according to claim 1, wherein said buffer is HEPES buffer.

3. The liquid pharmaceutical composition according to claim 1, comprising 2 mg/mL to 30 mg/mL anakinra.

4. The liquid pharmaceutical composition according to claim 1, wherein said at least one osmolyte is taurine.

5. The liquid pharmaceutical composition according to claim 1, wherein said at least one osmolyte is hydroxyproline.

6. The liquid pharmaceutical composition according to claim 1, further comprising one or more of a chelating agent, and a surfactant.

7. The liquid pharmaceutical composition according to claim 6, wherein said chelating agent is EDTA and said surfactant is polysorbate 80.

8. The liquid pharmaceutical composition according to claim 1, wherein the buffer stabilizes the pH of the composition at about 6.5.

9. The liquid pharmaceutical composition according to claim 1, wherein the concentration of said at least one osmolyte is adjusted to provide an isotonic composition.

10. The liquid pharmaceutical composition according to claim 9, wherein said composition has an osmolality of from 280 to 320 mOsmol/kg.

11. The liquid pharmaceutical composition according to claim 1, wherein the concentration of said at least one osmolyte is adjusted to provide a hypotonic composition.

12. The liquid pharmaceutical composition according to claim 11, wherein said composition has an osmolality of from 150 to 280 mOsmol/kg.

13. The composition according to claim 1, comprising
   2 mg/mL to 25 mg/mL anakinra;
   5 mM to 50 mM HEPES buffer, wherein said buffer stabilizes the pH of the composition at pH from 6 to 7;
   1 mg/mL to 100 mg/mL of an osmolyte selected from taurine and hydroxyproline, and
   0.1 mg/mL to 5 mg/mL NaCl.

14. The liquid pharmaceutical composition according to claim 1, comprising
   2 mg/mL to 25 mg/mL anakinra;
   5 mM to 50 mM HEPES buffer, wherein said buffer stabilizes the pH of the composition at pH from 6 to 7;
   1 mg/mL to 100 mg/mL of an osmolyte selected from taurine, proline, hydroxyproline, and mannitol;
   0.05 mM to 1 mM EDTA;
   0.01% to 1% polysorbate 80; and
   0.1 mg/mL to 5 mg/mL NaCl.

15. The liquid pharmaceutical composition according to claim 12, wherein said buffer is 10 mM HEPES buffer, which stabilizes the pH of the composition at about 6.5.

16. The liquid pharmaceutical composition according to claim 1, wherein said at least one osmolyte represents 15 mg/mL to 40 mg/mL taurine.

17. The liquid pharmaceutical composition according to claim 1, wherein said at least one osmolyte represents 20 mg/mL to 40 mg/mL taurine.

18. The liquid pharmaceutical composition according to claim 1, wherein said at least one osmolyte represents 20 mg/mL to 40 mg/mL hydroxyproline.

19. The liquid pharmaceutical composition according to claim 1, comprising
   5 mg/mL to 25 mg/mL anakinra;
   10 mM HEPES buffer, which stabilizes the pH of the composition at about 6.5;
   about 30 mg/mL taurine, and
   0.1 mg/mL to 5 mg/mL NaCl.

20. The liquid pharmaceutical composition according to claim 1, comprising
   5 mg/mL to 25 mg/mL anakinra;
   10 mM HEPES buffer, which stabilizes the pH of the composition at about 6.5;
   0.5 mM EDTA;
   0.1% Polysorbate 80;
   1 mg/mL to 1.5 mg/mL NaCl;
   about 30 mg/mL taurine, and
   0.1 mg/mL to 5 mg/mL NaCl.

21. The liquid pharmaceutical composition according to claim 19, comprising from about 15 mg/mL to about 25 mg/mL anakinra.

22. The liquid pharmaceutical composition according to claim 1, comprising
   2 mg/mL to 25 mg/mL anakinra;
   10 mM-50 HEPES buffer;
   15 mg/mL-25 mg/mL taurine, and
   0.1 mg/mL to 5 mg/mL NaCl.

23. The liquid pharmaceutical composition according to claim 1, comprising
   2 mg/mL to 25 mg/mL anakinra;
   10 mM-50 mM HEPES buffer; and
   15 mg/mL-25 mg/mL hydroxyproline.

24. A drug delivery device comprising a liquid pharmaceutical composition according to claim 1.

25. The device of claim 24, selected from a blow fill seal container, a single use container and a multi use container.

26. The liquid pharmaceutical composition according to claim 1, wherein said composition is stable under ambient conditions.

27. The liquid pharmaceutical composition according to claim 1, wherein said composition is stable after storage for a period of at least two weeks.

28. The liquid pharmaceutical composition according to claim 1, wherein said composition is stable at a temperature of 2° C. to 8° C., for a time period of at least one week.

29. The liquid pharmaceutical composition according to claim 1, wherein said composition is stable at a temperature of 2° C. to 15° C., for a time period of at least one week.

30. The liquid pharmaceutical composition according to claim 1, wherein said composition is stable at a temperature of at a temperature of 20° C. to 40° C., for a time period of at least two days.

31. The liquid pharmaceutical composition according to claim 1, wherein said composition further comprises an excipient suitable for topical administration.

\* \* \* \* \*